United States Patent [19]
Zuehlsdorf

[11] Patent Number: 5,222,510
[45] Date of Patent: Jun. 29, 1993

[54] DENTAL RING FLOSSER

[76] Inventor: Wayne L. Zuehlsdorf, 1269 Lansing Ave., Bremerton, Wash. 98312

[21] Appl. No.: 808,686

[22] Filed: Dec. 17, 1991

[51] Int. Cl.$^5$ ............................................. A61C 15/00
[52] U.S. Cl. ................................................... 132/323
[58] Field of Search ............... 132/321, 323, 324, 325, 132/326, 327

[56] References Cited

U.S. PATENT DOCUMENTS

| | | | |
|---|---|---|---|
| 1,110,680 | 9/1914 | Gamble | 132/325 |
| 1,217,779 | 2/1917 | Kleckner | 132/325 |
| 1,221,586 | 4/1917 | Powell | 132/323 |
| 2,451,181 | 10/1948 | Swartzman | 132/325 |
| 2,463,660 | 3/1949 | Turenchalk et al. | 132/327 |
| 4,615,349 | 10/1986 | Kukuruzinski | 132/323 |
| 4,638,824 | 1/1987 | De La Hoz | 132/323 |
| 4,729,392 | 3/1988 | Tenny | 132/323 |

Primary Examiner—John J. Wilson
Attorney, Agent, or Firm—Roy E. Mattern, Jr.; William G. Forster

[57] ABSTRACT

A dental hygiene instrument, called a dental ring flosser, is used to remove dental debris from between the teeth of the user. The dental ring flosser has an aperture sized to firmly and snugly fit around the end of a user's finger, so his or her finger may be solely used during flossing, to manipulate the strand of dental floss secured to the dental ring flosser. The strand of dental floss is adjustably supported on two alike opposing elongated spaced prongs formed integrally with the dental ring flosser. By adjusting the tension in the stand of dental floss, the finger ring size is adjusted so the dental ring flosser fits firmly and snugly about the user's finger.

18 Claims, 2 Drawing Sheets

DENTAL RING FLOSSER

BACKGROUND

The present invention relates to the general art of dental hygiene and, more particularly, to devices that hold and position dental floss between a person's teeth.

A common technique to remove debris between one's teeth is to stretch a strand of floss between the hands and manipulate the floss in and around the space between the teeth. This method, however, is awkward and, moreover, the user increases the risk of slippage and painful skin cuts. To eliminate such problems, inventors have developed a number of devices to hold and secure dental floss during the flossing operation.

One such early design by Chamberlin is disclosed in U.S. Pat. No. 2,784,722. The '722 patent incorporates an elongated handle attached to a forked shaped head. Floss is stretched across the two members that form the fork. One hand is required to perform the flossing operation. The elongated handle permits the user to reach the rearmost teeth without extending the hand into the mouth. The handle is designed to hold spare floss. This design, however, is somewhat bulky and requires the user to perform the flossing operation with the hand positioned some distance from the teeth. In this way, the user's sensitivity to the flossing operation is reduced. In addition, the design requires that the flossing operation be performed by using more than one finger.

A later design by Adams is disclosed in U.S. Pat. No. 3,696,821. The '821 design employs a pair of caps or thimbles to engage over two fingers on different hands of the user. Floss is stretched from one finger to the other. The thimbles frictionally clamp the dental floss to the fingers so that the floss may be properly tensioned for use without requiring that floss be wound around the finger tips. Like the Chamberlin design, the '821 patent requires a person to use more than one finger to floss, and further, the user is required to use both hands to perform the flossing operation.

Finally, a more recent design is disclosed by Yafai in U.S. Pat. No. 4,304,246. The Yafai apparatus incorporates a U-shaped frame that holds an endless loop of floss. The endless loop fits around the frame so that the floss extends across from one prong of the "U" to the other opposing prong. The user holds and manipulates the frame by clasping it between the thumb and forefinger. Like the Chamberlin device, the '246 apparatus is bulky and requires the user to employ more than one finger to accomplish the flossing operation. Also, the user's sensitivity to the flossing operation is similarly reduced.

The hygiene devices noted above all require two or more fingers to operate. In addition, all of these devices are bulky and reduce sensitivity to the flossing operation. Accordingly, a need remains for a flossing device that is simple, inexpensive, compact, easy and safe to use, and that can readily be adapted to use with only one finger.

SUMMARY

One object of the present invention is to enable a person to perform the dental flossing operation using only one finger on one hand, with his or her other hand not being used, when the tautly held dental floss is being moved down and up between all the teeth in a person's mouth.

A second object is to eliminate having to insert more than one finger into the mouth while flossing.

Another object is to eliminate the risk of painful skin cuts caused by dental floss slipping against the skin.

A further object is to have a compact device that will operatively position dental floss between the teeth in a user's mouth.

A further object is to reduce hand fatigue.

Yet another object is to aid dental floss users that have limited hand dexterity.

Still another object is to minimize the amount of dental floss required to clean the teeth.

A further object is to easily floss the rear spaces between the teeth.

The invention is a dental hygiene instrument that fits over a finger of the user and operates responsive to finger movement. The instrument removes dental debris lodged between teeth by holding, positioning, an manipulating dental floss between the user's teeth. The preferred embodiment of the invention employs an open-ended ring having two opposing prongs that extend outward from either side of the open section of ring. The floss is stretched from one prong to the opposing prong and is secured by tie posts disposed near the base of each prong. The prongs are positioned symmetrically on the open-ended ring thereby minimizing twisting when one finger is used in the flossing operation.

The ring's size can be altered by varying the tension in the floss. However, a modification to this design is a solid ring without an open section, manufactured in exact predetermined sizes, to fit children as well as adults.

The foregoing and other objects, features, and advantages of this invention will become more readily apparent from the following detailed description of a preferred embodiment which proceeds with reference to the accompanying drawings.

DETAILED DESCRIPTION OF PREFERRED READ

Figure 1:
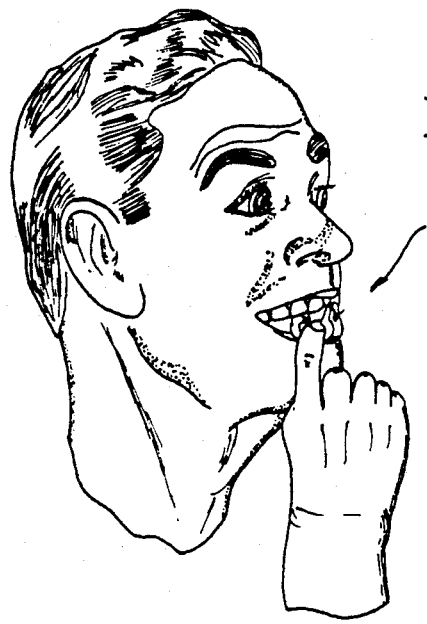
FIG. 1 is a perspective view of a preferred embodiment showing the use of this dental hygiene instrument, called a dental ring flosser constructed in accordance with the present invention.
Figure 2:
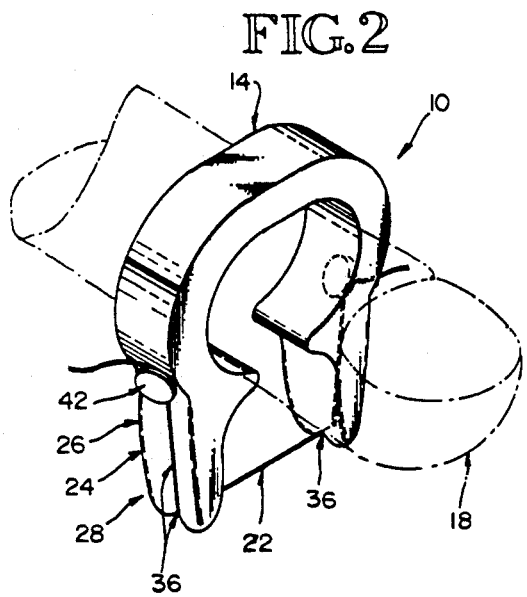
FIG. 2 is a perspective view of the dental ring flosser, its placement illustrating over a finger of the user.
Figure 3:
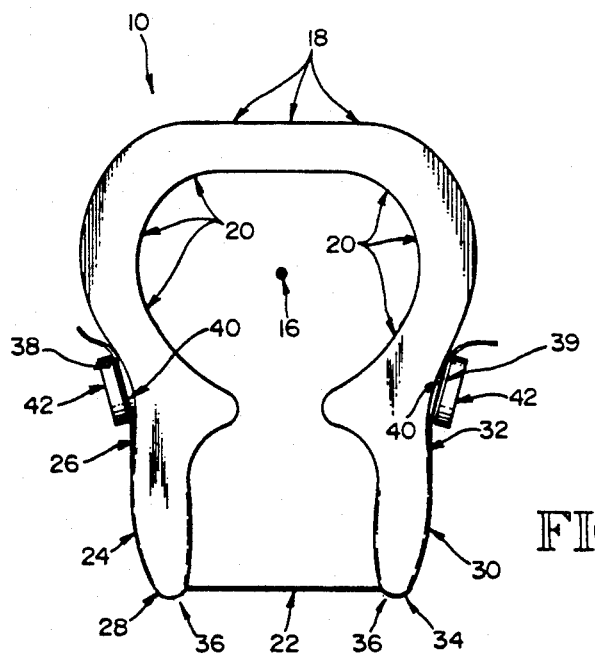
FIG. 3 is a elevational view of the preferred embodiment of a dental ring flosser.

Referring to the drawings, and first more specifically to FIGS. 1 through 5 is indicated generally a Dental Ring Flosser 10 constructed in accordance with the present invention.

Included therein is an open-ended ring 14 having an arcuate shape including a center 16, sized general to firmly and snugly fit the end of a person's finger 12 which is generally the user's index finger, as shown in FIG. 1. This index finger is the only finger manipulated by the person moving the tautly held dental strand of floss down and up between his or her teeth. The person's other hand is not used during these down and up cleaning motions. Attached thereto is a first prong 24 and a second for holding a strand of dental floss 22 in an operative position. The dental floss 22 is stretched across the prongs and secured to a first tie post 38 and a second tie post 39 by coiling the floss 22 around the same.

Considering now in more detail the components that comprise a Dental Ring Flosser 10, the open ended ring 14 includes a radially-outer surface 18 and a radially-inner surface 20. The radially-inner surface 20 conforms closely over a human finger 12 and remains in close contact with the the finger 12 during the flossing operation. The radially-outer surface 18 provides a surface to which the first prong 24 and the second prong 30 are attached.

More specifically, the first prong 24 has a first end 26 fixedly attached to the radially-outer surface 18 and a second end 28 that will later be more fully explained. Similarly, the second prong 30 has a first end 32 fixedly attached to the radially-outer surface 18 and a second end 34. The first prong 24 and second prong 30 are disposed substantially symmetrically about an axis bisecting the center 16 of the open-ended ring 14. The prongs are so disposed to minimize twisting of the open-ended ring 14 around the finger 12 when only one finger is used during the flossing operation.

The second end 28 of the first prong 24 and the second end 34 of the second prong 30 are spaced apart and adapted to receive the dental floss 22. During the flossing operation, the dental floss 22 spans from the second end 28 of the first prong 24 to the second end 34 of the second prong 30.

Figure 4:
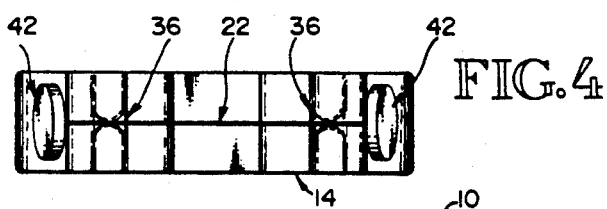
FIG. 4 is a bottom view of the dental ring flosser.
Figure 5:
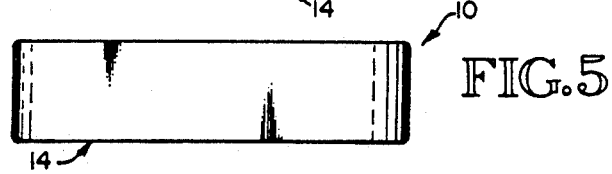
FIG. 5 is a plan view of the dental ring flosser.

Referring now to FIG. 4, a groove 36 is illustrated as a means to engage the floss 22. Generally, the groove 36 is disposed in parallel relation to a plane defined by the open-ended ring 14. More specifically, the groove is aligned in the direction of the floss thereby preventing lateral slippage, i.e., slippage in a direction normal to the floss 22 from the prong ends, 28 and 34, of the two prongs 24 and 30. The floss 22 is lodged in the groove 36 by stretching it from the prongs, as noted above, and securing it to first and second opposing tie posts, 38 and 38. To secure the floss 22, each tie post includes a rod 40 to coil the floss 22 around, and a flanged end 42 to prevent the floss 22 from disengaging the rod.

In operation, the floss advances from a first tie post 38, through a groove 36 of the second end 28 of the first prong 24 to the second end 34 of the second prong 30, and similarly through a corresponding groove 36, then to the opposing second tie post 39. To maintain tension in the floss 22, the floss 22 is coiled around the rod 40 of each tie post, 38 and 39.

Because the open-ended ring is constructed of a resilient material, such as plastic, the opening of the open-ended ring 14 changes responsive to varying tension in the floss 22. In this way, a user can easily adjust the size of the open-ended ring 14 by adjusting the tension in the floss 22. Likewise, pressure between the user's finger 12 and the radially-inner surface 16 of the open-ended ring 14 can be controlled. Accordingly, slippage of the open-ended ring 14 from a user's finger 12 can be reduced by controlling the friction created from such pressure. A ring 14 so constructed is inexpensive and easily produced by molds that can be reused numerous times.

Figure 6:
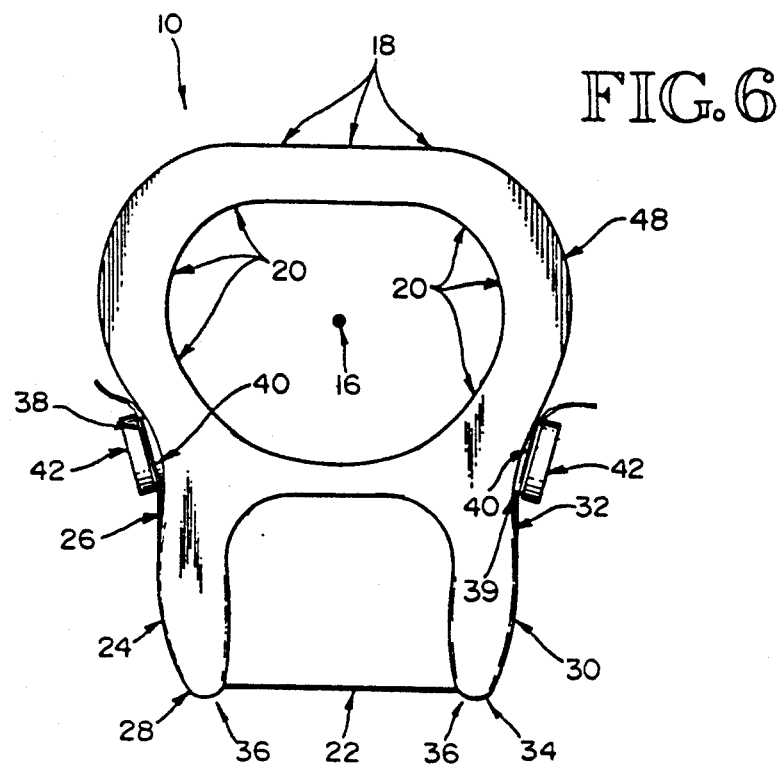
FIG. 6 is a elevational view of a another embodiment of the dental ring flosser formed as a complete ring instead of an open-ended ring.

FIG. 6 illustrates a modification of the invention wherein a solid endless ring 48 replaces the open-ended ring 14. Here, a Dental Ring Flosser 10 is constructed using a solid endless ring 48 having a radially-inner surface 20 and a radially-outer surface 18. In all other respects, the Dental Ring Flosser 10 is unchanged. The floss 20 is threaded in a similar manner described in the foregoing. Because the modified endless ring 48 is solid, the size of the Dental Ring Flosser 10 is not adjustable responsive to tension in the floss 22. Thus the solid endless ring Dental Ring Flosser 10 is constructed in predetermined sizes according to the size of a user's finger 12.

Figure 7:
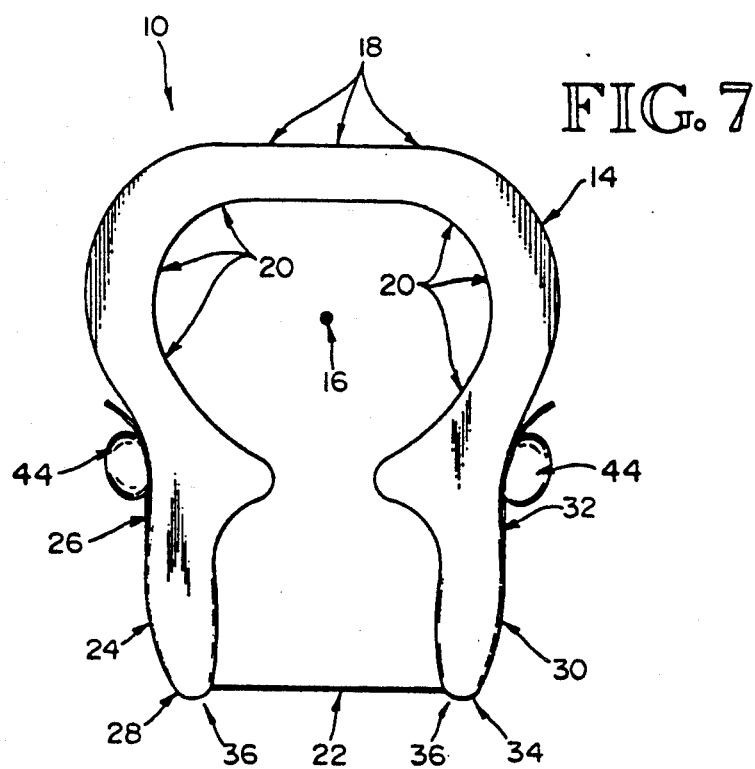
FIG. 7 is a elevational view of another embodiment of the dental ring flosser formed as an open-end ring and having spherical lugs used in anchoring the ends of the taut dental floss, instead of having the tie posts used in anchoring the ends of the taut dental loss, as shown in FIGS. 2, 3, 4 and 6.

FIG. 7 illustrates a further modification of the invention wherein a substantially spherical lug 44 replaces the first and second tie posts, 38 and 39, to secure the dental floss 22. Here, the Dental Ring Flosser 10 is constructed with an open-ended ring 14, as previously illustrated, having a first prong 24 and a second prong 30 fixedly attached thereto. As noted above, dental floss 22 is stretched from one prong to an opposing prong. The modification adapted herein consists of a substantially spherical lug 44, replacing the tie posts 38 and 39, to secure the floss 22 to the Dental Ring Flosser 10. The lugs 44 are attached in the general area where the first end of the first prong 26 and the first end of the second prong 32 are attached to the open-ended ring 14. The floss 22 is secured by coiling it around the respective lugs 44.

Having illustrated and described the principles of my invention in a preferred embodiment thereof, it should be readily apparent to those skilled in the art that the invention can be modified in arrangement and detail without departing from such principles.

I claim all modifications coming within the spirit and scope of the accompanying claims.

1. A dental hygiene instrument, called a dental ring flosser, used when removing dental debris from between the teeth of a user, comprising:
    (a) an aperture means which is an open-ended ring having a radially-inner surface and a radially-outer coaxial surface, wherein the open-ended ring is formed of resilient material and defines a plane, and by adjusting the tension in the strand of the dental floss, the finger ring size is adjusted, so the dental ring flosser fits firmly and snugly about the user's finger, so only one finger is used in manipulating this dental ring flosser,
    (b) a strand of dental floss; and
    (c) positioning means, for tautly holding the said strand of dental floss, for subsequent down and up movement between the teeth of a user is fixedly attached to said aperture means symmetrically about an axis bisecting the said aperture means.

2. A dental hygiene instrument, called a dental ring flosser, as recited in claim 1, wherein the positioning means comprises a first and a second elongated prong of similar size and shape, each elongated prong having a first end and a second end.

3. A dental hygiene instrument, called a dental ring flosser, as recited in claim 2, wherein the first end of the first elongated prong is fixedly attached to the radially-outer surface of the open-ended ring, and the first end of the second elongated prong is fixedly attached to the radially-outer surface of the open-ended ring.

4. A dental hygiene instrument, called a dental ring flosser, as recited in claim 3, wherein the first and second elongated prongs define a plane parallel to the plane defined by the open-ended ring.

5. A dental hygiene instrument, called a dental ring flosser, as recited in claim 2, wherein a groove is formed in the second end of the first and second prong.

6. A dental hygiene instrument, called a dental ring flosser, as recited in claim 5, wherein the groove is parallel to a plane defined by the open-ended ring.

7. A dental hygiene instrument, called a dental ring flosser, as recited in claim 2, further comprising means for securing the strand of dental floss from the second end of the first prong to the second end of the second prong.

8. A dental hygiene instrument, called a dental ring flosser, as recited in claim 7, wherein the means for securing the strand of dental floss, comprises a first and a second tie post disposed on the radially-outer surface of the open-ended ring for engaging the dental floss.

9. A dental hygiene instrument, called a dental ring flosser, as recited in claim 8, wherein the first and second tie post each comprise a rod having a flanged end to prevent the strand of dental floss from disengaging.

10. A dental hygiene instrument, called a dental ring flosser, as recited in claim 7, wherein means for securing the strand of dental floss comprises a first and second lug disposed on the radially-outer surface of the open-ended ring for tightly engaging the strand of dental floss.

11. A dental hygiene instrument, called a dental ring flosser, as recited in claim 10, wherein the first and second lugs are substantially spherical in shape.

12. A dental hygiene instrument, called a dental ring flosser for removing food particles and debris from between the teeth of a user, comprising:
   (a) an endless ring having a center, a radially-inner surface, and a radially-outer coaxial surface, sized to firmly and snugly fit around the end of a user's finger so his or her finger may be used to manipulate the dental ring flosser;
   (b) a strand of dental floss; and
   (c) positioning means for tautly holding the said strand of dental floss is fixedly attached to the endless ring and is symmetrical about an axis bisecting the center of the endless ring, and
   wherein the positioning means comprises a first and second elongated prong of similar size and shape, each elongated prong having a first and second end.

13. A dental hygiene instrument, called a dental ring flosser, as recited in claim 12, wherein the first end of the first elongated prong is fixedly attached to the radially-outer surface of the endless ring, and the first end of the second elongated prong is fixedly attached to the radially-outer surface of the endless ring.

14. A dental hygiene instrument, called a dental ring flosser, as recited in claim 13, wherein a groove sis formed in the second end of the first and second prong parallel to a plane defined by the endless ring.

15. A dental hygiene instrument, called a dental ring flosser, as recited in claim 12, further comprising means for securing the strand of the dental floss to the endless ring.

16. A dental hygiene instrument, called a dental ring flosser, as recited in claim 15, wherein means for securing the strand of the dental floss comprises a first and a second tie post disposed on the radially-outer surface of the endless ring for securing the strand of the dental floss.

17. A dental hygiene instrument, called a dental ring flosser, as recited in claim 16, wherein the first and second tie post comprise a rod having a flanged end to prevent the strand of the dental floss from disengaging.

18. A dental hygiene instrument, called a dental ring flosser, for removing food particles debris between the teeth of a user, comprising:
   (a) an open-ended ring having a center, a radially-inner surface, and a radially-outer coaxial surface, wherein the open-ended ring is formed of resilient material, and sized to firmly and snugly fit around the end of a person'finger;
   (b) a strand of dental floss;
   (c) a first and second elongated prong of similar size and shape, each elongated prong having a first end and a second end, the first end of each prong being fixedly attached to the radially-outer surface of the open-ended ring, and these first and second elongated prongs are symmetrical about an axis bisecting the center of the open-ended ring; and
   (d) securing means for tautly holding the strand of dental floss, extending from the second end of the first prong to the second end of the second prong, and whereby, by adjusting the tension in the strand of the dental floss, the finger ring size is adjusted, so the dental ring flosser fits firmly and snugly about the user's finger, so only one finger is used in manipulating this dental ring flosser.

* * * * *